US005565630A

United States Patent [19]

Shene

[11] Patent Number: 5,565,630
[45] Date of Patent: Oct. 15, 1996

[54] PEAK FLOW METER

[75] Inventor: William R. Shene, Plattsburgh, N.Y.

[73] Assignee: Monaghan Medical Corporation, Plattsburgh, N.Y.

[21] Appl. No.: 438,156

[22] Filed: May 11, 1995

Related U.S. Application Data

[63] Continuation-in-part of Ser. No. 344,530, Nov. 23, 1994, which is a continuation of Ser. No. 153,091, Nov. 17, 1993, abandoned.

[51] Int. Cl.⁶ .................................. G01F 1/28; G01F 1/22
[52] U.S. Cl. .......................................... 73/861.76; 128/727
[58] Field of Search ........................... 73/861.53, 861.54, 73/861.55, 861.56, 861.58, 861.71, 861.74, 861.76; 128/725, 727; 116/273, 272, 264

[56] References Cited

U.S. PATENT DOCUMENTS

| | | |
|---|---|---|
| D263,166 | 3/1882 | Bushman . |
| 471,389 | 3/1892 | Lacey ..................... 128/727 |
| 599,746 | 3/1898 | St. John ................ 73/861.58 |
| 1,541,750 | 6/1925 | Park ............................ 73/17.9 |
| 2,061,852 | 11/1936 | Schweitzer ........... 73/861.58 |
| 3,298,362 | 1/1967 | Lippitt, Jr. et al. ....... 128/668 |
| 3,635,214 | 1/1972 | Rand et al. ............... 128/727 |
| 3,681,986 | 8/1972 | Wyatt ..................... 73/861.12 |
| 3,719,083 | 3/1973 | Morris et al. .......... 73/204.14 |
| 3,720,202 | 3/1973 | Cleary ....................... 128/727 |
| 3,722,278 | 3/1973 | Young et al. .......... 73/861.71 |
| 3,797,480 | 3/1974 | Williams .................. 128/724 |
| 3,826,247 | 7/1974 | Ruskin et al. ............ 128/727 |
| 3,862,628 | 1/1975 | Williams .................. 128/727 |
| 3,940,984 | 3/1976 | Oram .................... 73/170.15 |
| 3,958,565 | 5/1976 | Wright ..................... 128/727 |
| 4,019,382 | 4/1977 | El-Gammal ........... 73/861.39 |
| 4,041,935 | 8/1977 | Garbe ....................... 128/727 |
| 4,050,303 | 9/1977 | Hemp et al. ........... 73/861.12 |
| 4,078,428 | 3/1978 | Baker et al. ........... 73/861.31 |
| 4,196,621 | 8/1980 | Beese et al. ........... 73/861.22 |

(List continued on next page.)

FOREIGN PATENT DOCUMENTS

| | | |
|---|---|---|
| WO93/07778 | 4/1993 | European Pat. Off. . |
| 267933 | 6/1927 | United Kingdom . |
| 1160669 | 8/1969 | United Kingdom . |

OTHER PUBLICATIONS

Advertisement for "Assess Peak Flow Meter", believed to be published prior to Nov. 17, 1993.
Advertisement for "Personal Best Flow Meter", believed to be published prior to Nov. 17, 1993.
Advertisement for "Astech Peak Flow Meter", believed to be published prior to Nov. 17, 1993.
Photographs of "Pocketpeak" peak flow meter manufactured by Ferraris Medical Ltd. Believed to be known or used prior to Nov. 17, 1993.
Photographs of "SPIR–O–Flow" peak flow meter manufactured by Spirometrics, Inc. Believed to be known or used prior to Nov. 17, 1993.
Photographs of peak flow meter manufactured by Ferraro's Medical Ltd. believed to have been known or used prior to May 11, 1995.
Copy of instruction manual for "SPIRA" peak flow meter believed to have been published prior to May 11, 1995.
Copy of instruction manual for "ASSESS" peak flow meter manufactured by Healthscan Products, Inc., dated Aug. 1991.
Copy of instruction manual for "Personal Best" peak flow meter manufactured by Healthscan Products, Inc. dated 1994.

(List continued on next page.)

*Primary Examiner*—Richard Chilcot
*Assistant Examiner*—Harshad Patel
*Attorney, Agent, or Firm*—Brinks Hofer Gilson & Lione

[57] ABSTRACT

An improved peak flow meter for measuring the peak flow of exhaled air including an indicator and one or a plurality of vents designed so that the indicator provides a logarithmic measurement of the exhaled air. Also provided is a peak flow meter adaptable for low and high flow rate applications.

20 Claims, 6 Drawing Sheets

5,565,630

Page 2

U.S. PATENT DOCUMENTS

| | | | |
|---|---|---|---|
| 4,259,967 | 4/1981 | Vooren et al. | 128/720 |
| 4,292,775 | 9/1981 | Hutton | 73/861.79 |
| 4,292,853 | 10/1981 | Williams et al. | 73/861.79 |
| 4,294,262 | 10/1981 | Williams et al. | 128/726 |
| 4,421,120 | 12/1983 | Edwards, Jr. et al. | 128/725 |
| 4,533,137 | 8/1985 | Sonne | 128/225 |
| 4,638,812 | 1/1981 | Hakkinen | 73/661.76 |
| 4,640,293 | 2/1987 | Garbe et al. | 128/716 |
| 4,768,520 | 9/1988 | Varraux et al. | 128/725 |
| 4,944,306 | 7/1990 | Alvino | 128/725 |
| 4,967,596 | 11/1990 | Rilling et al. | 73/492 |
| 5,246,010 | 9/1993 | Gazzara et al. | 128/725 |

OTHER PUBLICATIONS

Advertisement of Vitalograph peak flow meter from Apr./May 1994 "Journal of Respiratory Care Practitioners".

Copy of pamphlet entitled "Peak Flow Monitoring for Patients With Asthma", published by HealthScan Inc., dated 1990.

Manual entitled "Peak Performance A Strategy for Asthma Self–Assessment", by Guillermo R. Mendoza, M.D., dated 1987.

PEAK FLOW METER

REFERENCE TO RELATED APPLICATIONS

This application is a continuation-in-part of application Ser. No. 08/344,530 filed Nov. 23, 1994, entitled "Peak Flow Meter" which is a continuation of application Ser. No. 08/153,091, filed Nov. 17, 1993, now abandoned. The aboveidentified applications, in their entirety, are incorporated herein by reference.

BACKGROUND OF THE INVENTION

This invention relates to an improved peak flow meter. Peak flow meters are used for measuring the peak air flow of a patient's exhalation. Peak flow meters permit physicians to track changes in the patient's respiratory condition and diagnose potential or existing breathing problems. Patients also use peak flow meters outside a doctor's office to monitor their own condition on a regular basis.

Existing peak flow meters provide various ways of measuring peak air flow. For example, U.S. Pat. No. 4,421,120 discloses a peak respiratory flow monitor with multiple openings and a reed that generates a sound when air flow reaches an adjustable threshold. While the device disclosed in the '120 patent is relatively simple to use and indicates a peak flow threshold, it does not provide detailed measurement readings to a patient.

An example of a peak flow meter providing more detailed information to a user is U.S. Pat. No. 5,246,010. As is common with mechanical peak flow meters, the '010 patent discloses a peak flow meter with an indicator responsive to internal pressure as generated by peak air flow. Three adjustable markers are adjacent to a scale along which the indicator moves. A personal zone calculator for determining where to place the adjustable markers is provided. Although the '010 patent provides patients with more detailed information, it is relatively complicated to set up and use.

Accordingly, there is a need for a peak flow meter that provides detailed, accurate information and is simple to set up and use.

SUMMARY OF THE INVENTION

The present invention provides for an improved peak flow meter for use by doctors and patients. An embodiment of the present invention includes a peak flow meter having a hollow body to accommodate a flow of exhaled air. An indicator is associated with the body and is movable to a position along a scale on the body. The position along the scale is related to the peak air flow passed through the hollow body of the peak flow meter. The hollow body has at least one vent, and preferably a plurality of vents, designed so that the indicator's position in response to the peak flow of exhaled air conforms to a logarithmic scale on the body.

According to another aspect of this invention, a peak flow meter is provided that is adaptable for use in measuring low flow rates, such as peak flow of a young child's exhalation. The adaptable peak flow meter includes a bias vent for altering flow measurement capability. In one embodiment, the peak flow meter has a removable snap-fit window designed to fit in a window slot in the body of the peak flow meter.

An assessment tape attachable to a peak flow meter is disclosed for use in determining respiratory performance. In one embodiment the tape has a plurality of colored zones representing fixed percentage deviations below any point along a logarithmic scale on the peak flow meter, thereby eliminating the need for a calculator as shown in the prior art.

DETAILED DESCRIPTION OF THE PRESENTLY PREFERRED EMBODIMENTS

Figures 1, 2, 3, 4, 5, 6:
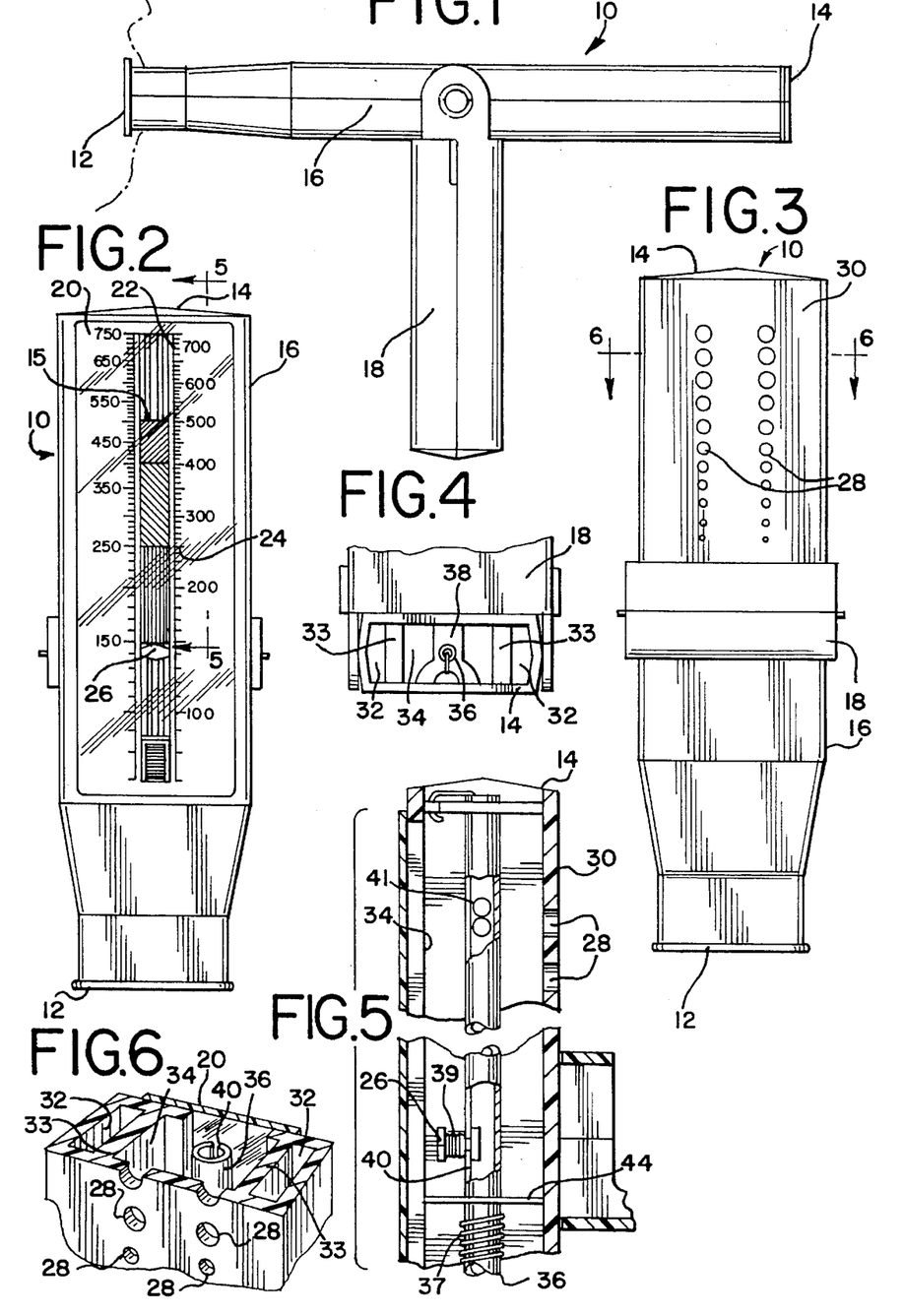
FIG. 1 is a side view of a peak flow meter in accordance with a preferred embodiment of the present invention.
FIG. 2 is a top view of the peak flow meter of FIG. 1.
FIG. 3 is a bottom view of the peak flow meter of FIG. 1.
FIG. 4 is a fragmentary end view of the peak flow meter of FIG. 1.
FIG. 5 is a magnified cross-sectional view taken along line 5—5 of FIG. 2.
FIG. 6 is a cross-sectional view taken along line 6—6 of FIG. 3.

FIGS. 1–6 illustrate a preferred embodiment of a peak flow meter 10. FIG. 1 shows a peak flow meter 10 with a body 16 having an inlet 12 and an outlet 14. The peak flow meter 10 also has a handle 18 for a patient using the device. As seen in greater detail in FIG. 2, the peak flow meter 10 has a window slot 22 in the body 16 covered by a clear window 20. The window slot 22 and window permit view of an indicator 26 mounted inside the body 16 that is movable with respect to the body longitudinally between the inlet 12 and outlet 14. Adjacent to the window slot 22 is a logarithmic scale 24 against which the position of the indicator 26 may be measured. In one preferred embodiment, the logarithmic scale 24 may be printed or integrally molded onto the body 16. In another preferred embodiment, the logarithmic scale 24 may be printed or integrally molded onto the window 20. The body 16 and window 20 are preferably made of a plastic material.

A logarithmic scale, as is inherent in its defined mathematical nature, provides greater intervals between measurement marks at the lower end of the scale and progressively smaller intervals at the higher end. A logarithmic scale 24 is preferable on a peak flow meter because the scale is compressed toward the high end where small variations in peak flow are less critical and expanded at the low end where small variations are more important. Also, young children produce less peak flow than adults so the expanded lower end scale provides younger users with an even easier scale to read.

An advantage of the logarithmic scale used in presently preferred embodiments is that simple assessment tapes may be used to aid in assessing an individual patient's condition. FIG. 2 illustrates a preferred embodiment of an assessment tape 15. The assessment tape 15 comprises a single colored strip having a plurality of translucent color zones. The tape may be mounted directly on the window 20. A preferred means of attachment is an adhesive coating on one side of the tape. Preferably, the assessment tape has three color zones in colors such as green, yellow and red. Each color zone indicates a fixed percentage range below a reference best value as established by a physician.

The window 20, in another preferred embodiment may be a removable snap-on window. The window 20 may be wide enough to cover the window slot 22 and portions of the body 16 surrounding the window slot or may simply fit into the window slot. A snap-on window allows for a patient to mount an assessment tape 15 underneath the window 20 to further insure that the assessment tape is not inadvertently dislodged.

FIG. 3 best shows the plurality of vents 28 on the bottom 30 of the peak flow meter 10. The peak flow meter 10 may have one, and preferably more than one, vent. The vents 28 extend longitudinally along the bottom 30 of the peak flow meter 10 and increase in size from the inlet 12 to the outlet 14. Preferably, the vents 28 are circular. The vents 28 may also be any shape or combinations of shapes in another preferred embodiment. Alternatively, the vents 28 may comprise one or more slots increasing in size from the inlet 12 to the outlet 14. Regardless of the type of vent 28 employed, the plurality of vents 28 are empirically designed to tailor the response of the peak flow meter 10 to a patient's forcible exhalation such that the indicator's 26 movement conforms to the logarithmic scale 24.

FIGS. 4 and 6 best illustrate a preferred multiple channel design of a presently preferred embodiment. The peak flow meter 10 preferably includes a sample channel 34 and at least one bypass channel 32 parallel to the sample channel 34. Air exhaled into the inlet 12 is divided between the sample and bypass channels 34, 32. The sample channel 34 is configured to accept a predetermined percentage of the air and the remaining air passes through the bypass channels 32.

FIG. 6 illustrates the position of the vents 28 with respect to the channels. The vents 28 preferably connect the sample channel 34 to the ambient air directly outside the body 16. In another preferred embodiment, the vents 28 are positioned in the walls 33 between the channels 32, 34 inside the body 16. The internal vents 28 provide the added advantage of avoiding accidental blockage in addition to the logarithmic measurement response.

FIGS. 4–6 show a hollow slotted tube 36 extending longitudinally through the sample chamber 34 inside the peak flow meter. The hollow slotted tube 36 is attached to a central support 38 at each end of the peak flow meter 10. The indicator 26 is preferably slidably mounted in a slot 40 in the tube 36. A piston 44 for releasably engaging the indicator 26 is also slidably mounted on the tube 36 between the inlet 12 and the indicator 26. The circumference of the piston 44 is less than the inner circumference of the body 16. A spring 37 attaches the piston 44 to the inlet end of the hollow tube 36 and retracts the piston 44 after a patient exhales into the peak flow meter 10.

A patient using the peak flow meter exhales forcibly into the inlet. The burst of exhaled air pushes against the piston which, in turn, pushes the indicator. The indicator stops at a point along the hollow tube where the force exerted on the piston 44 by the spring 37 substantially equals the force of the exhaled air remaining in the body. In order to obtain the preferred logarithmic response, the plurality of vents allow empirically determined amounts of exhaled air to escape the hollow body 16 so that the indicator's position conforms to the logarithmic scale 24. A position spring 39 keeps the indicator in place when the piston retracts.

After reading the position of the indicator along the logarithmic scale, the patient returns the indicator to its initial position by holding the outlet end and shaking the peak flow meter. A return mass 41, preferably a pair of ball bearings, mounted in the hollow slotted tube between the indicator and the outlet end assists in returning the indicator to its initial reset position. The return mass does not restrict the movement of the piston and indicator because the exhaled air also separately pushes the mass along the tube.

In an alternative embodiment, the walls of the sample channel may be empirically designed to nonlinearly curve outward from the inlet to the outlet. The outward curve of the walls causes an increasing gap to develop between the edge of the piston and the walls as exhaled air forces the piston along the sample chamber. The increasing gap increases the amount of exhaled air necessary to move the indicator and is empirically designed so that the indicator's movement conforms with a logarithmic scale. Non-linearly expanding walls and a plurality of vents may also be used in combination to achieve the desired indicator response.

FIGS. 7–10 set forth an improved peak flow meter 50 according to a second preferred embodiment of the present invention. The peak flow meter 50 includes a vertical section 52 attached to a horizontal section 54. The horizontal section has an inlet 58 and an outlet 60 for passing exhaled air through a bypass channel 76. The bypass channel is connected to a sample channel 72 inside the vertical section 52.

Figures 7, 8:
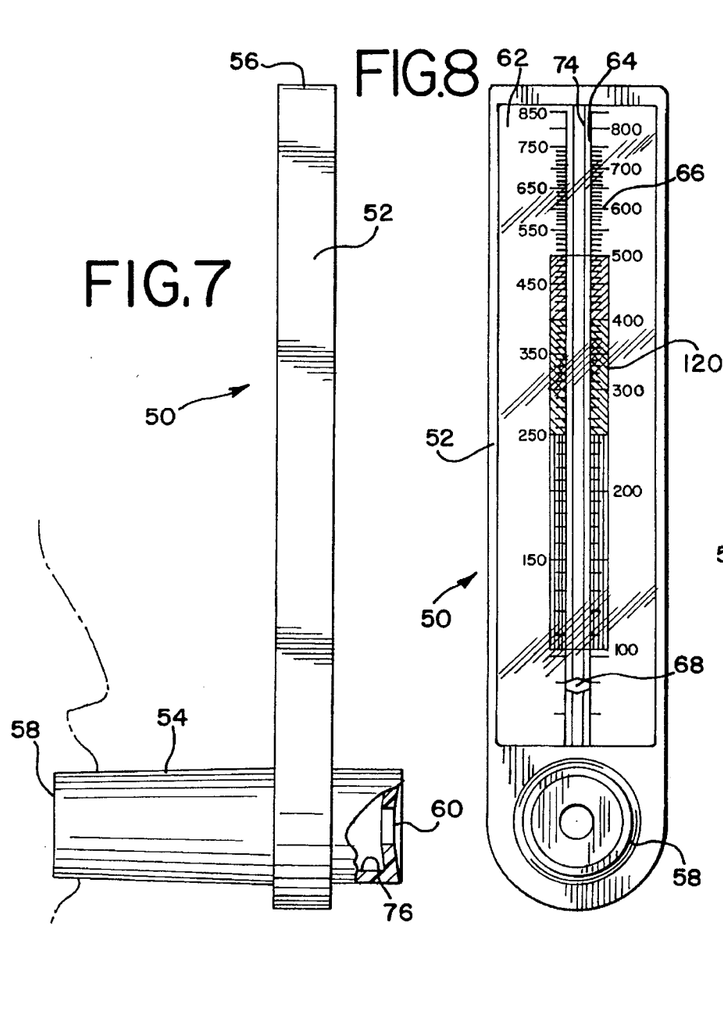
FIG. 7 is a side view of a second embodiment of a peak flow meter according to the present invention.
FIG. 8 is a front view of the peak flow meter at FIG. 7.

As shown in FIG. 8, the peak flow meter 50 has a window slot 64 in the vertical section 52. The window slot 64 is covered by a window 62. Preferably the window 62 is constructed of clear plastic. Adjacent to the window slot 64 is a logarithmic scale 66. Inside the vertical section 52 and visible through the window 62 is an indicator 68 slidably mounted on a hollow tube 74 extending longitudinally along the sample channel 72.

Figures 9, 10:
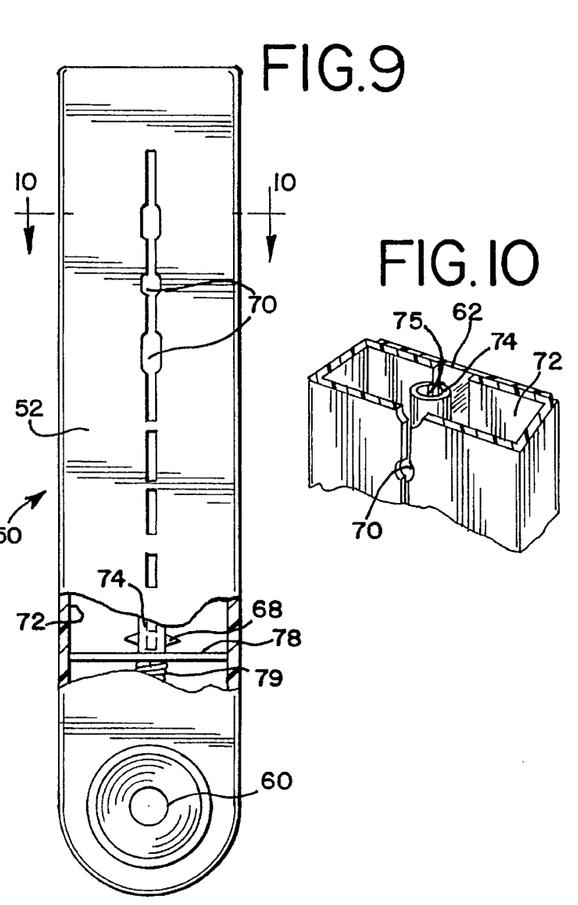
FIG. 9 is a fragmentary back view of the peak flow meter of FIG. 7.
FIG. 10 is a fragmentary cross-sectional view taken along line 10—10 of FIG. 9.

FIG. 9 illustrates the plurality of vents 70 positioned on the vertical section 52 of the peak flow meter. The vents 70 are designed such that the indicator 68 moves to a position corresponding to a logarithmic measure of a peak flow of air exhaled into the inlet 58. The vents 70 preferably increase in size from the portion of the vertical section 52 connected to the horizontal section to the vertical section outlet 56.

FIGS. 8–10 show the hollow tube 74 inside the sample channel 72. Preferably, the indicator 68 is slidably mounted in a slot 75 in the tube 74. When a patient exhales into the inlet 58 of the peak flow meter 50, the exhaled air passes through the bypass channel 76 and a portion flows through the sample channel 72.

The vents 70 in the sample channel 72 increase the force needed to move the indicator by allowing progressively more air to exit the sample channel 72 as the indicator moves along the tube 74. The increase in force required to move the indicator is empirically designed so that the final position of the indicator corresponds to a logarithmic scale measuring the peak air flow. The logarithmic relation allows a logarithmic scale 66 to be used having the advantages set forth above. When a patient exhales into the peak flow meter, the exhaled air received in the sample channel 72 pushes a piston 78 against the indicator 68. The piston pushes the indicator 68 along the tube 74 until the return force of the spring 79 overcomes the force of the exhaled air remaining in the sample channel.

Figure 17:
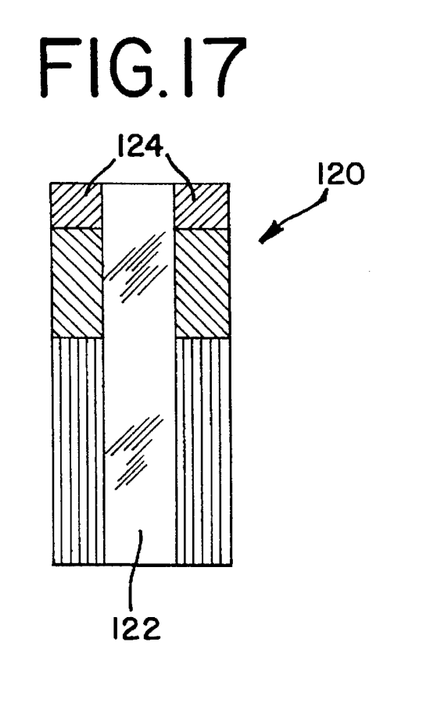
FIG. 17 is a top view of an assessment tape for use with a peak flow meter.

An alternative embodiment of an assessment tape for use with the peak flow meter is shown in FIG. 17. The tape 120 is preferably a single piece having a pair of colored strips 124 parallel to a clear central strip 122. The colored strips 124 preferably include at least two color zones. As shown in FIG. 8, an assessment tape 120 is preferably adhesively attached on the window over the logarithmic scale 66. Typically a doctor will measure a patient's peak flow and the doctor or patient will then apply the tape 120 to the peak flow meter 50. The color zones on the tape represent fixed percentages from measured peak flow. Because the plurality of vents on the peak flow meter 50 are designed so that a logarithmic scale 66 may be used, the tape 120 may be manufactured so that each color zone not only represents a fixed percentage from a particular peak value, but also represents the same fixed percentage of any peak value anywhere on the scale. A single tape which can be attached anywhere on the scale without adjustment permits any patient to use it. Further, a single adhesive tape having multiple zones is simple to attach and less likely to be accidentally moved by a user.

Figures 11, 12, 13, 14, 15, 16:
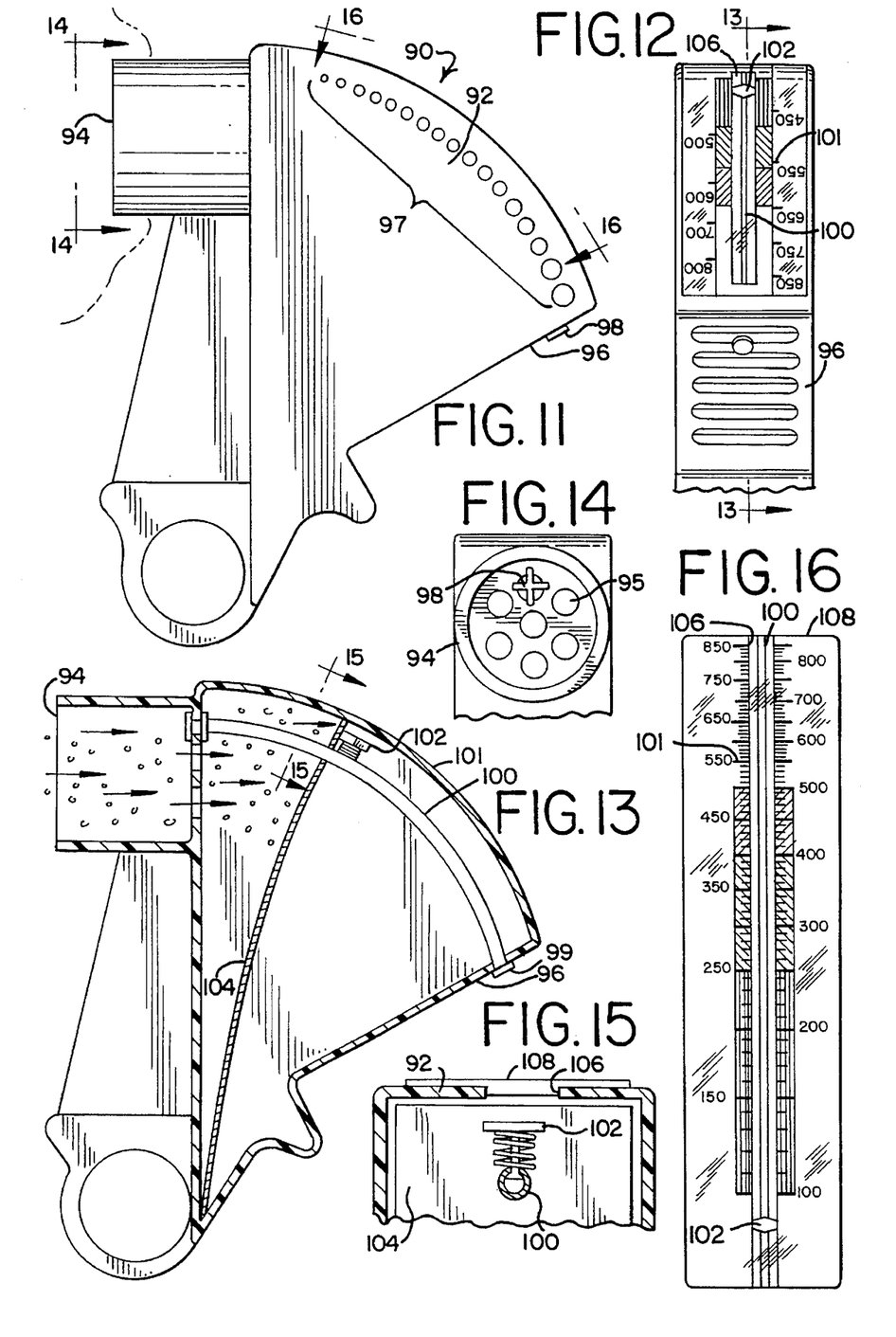
FIG. 11 is a side view of a third embodiment of a peak flow meter in accordance with the present invention.
FIG. 12 is a fragmentary back view of the peak flow meter of FIG. 11.
FIG. 13 is a cross-sectional view taken along line 13—13 of FIG. 12.
FIG. 14 is a fragmentary front view taken along line 14—14 of FIG. 11.
FIG. 15 is a fragmentary cross-sectional view taken along line 15—15 of FIG. 13.
FIG. 16 is a view taken along line 16—16 of FIG. 11.

A third preferred embodiment of an improved peak flow meter 90 is shown in FIGS. 11–16. FIG. 11 shows a peak flow meter 90 having an inlet 94 and an outlet area 96 on a curved hollow body 92. The body 92 also contains vents 97 along the side of the body 92 that increase in size from the inlet side to the outlet side. FIG. 12 illustrates the outlet portion 96 of the peak flow meter 90 and the logarithmic scale 101, window slot 106, and window 108. Underneath the window 108, an indicator 102 is slidably mounted on a hollow tube 100.

The interior of the hollow body 92 is best seen in FIG. 13. The inlet 94 receives exhaled air from a patient. The exhaled air pushes a bendable vane 104 against the indicator 102 slidably mounted on the hollow tube 100. As shown in FIG. 14, the inlet 94 contains air passageways 95 and an anchor 98 for the hollow tube 100. The hollow tube is attached to the outlet portion 96 by an exterior anchor 99. FIG. 15 shows the bendable vane 104 behind the indicator 102 inside the body 92 of the peak flow meter 90. The hollow tube 100 passes through the bendable vane 104 such that the vane 104 can push the indicator 102 along the tube 100 under the force of exhaled air.

Directly above the tube 100 is the window slot 106 and window 108. As seen in FIG. 16, the window 108 covers the window slot 106 so that a stray finger cannot interfere with the motion of the indicator 102. As with the embodiments shown in FIGS. 1–10, the embodiment in FIGS. 11–16 also employs a logarithmic scale 101 as a result of the vents 97 providing predetermined logarithmic response.

Figure 18:
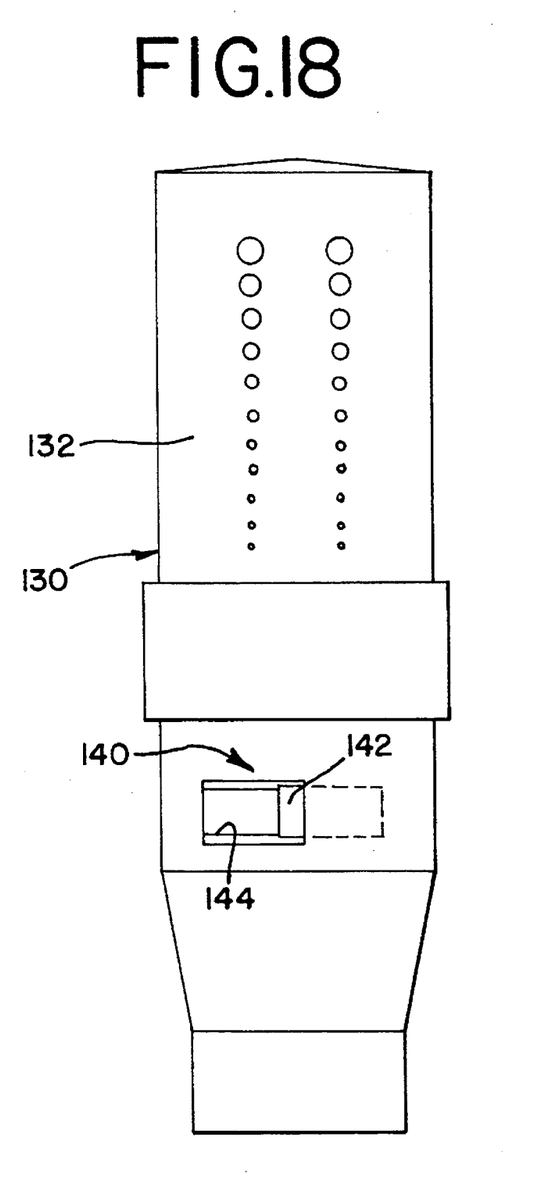
FIG. 18 is a bottom view of the peak flow meter of FIG. 3 adapted for high and low flow rate measurement.

FIG. 18 illustrates an improved peak flow meter 130 according to yet another alternative embodiment of the invention. This embodiment is adjustable to measure high or low flow rates. The peak flow meter 130 shown in FIG. 18 is a modification of the peak flow meter of FIGS. 1–6. A bias vent 140 is positioned on the body 132 of the peak flow meter 130. Preferably, the bias vent 140 is a slot 144 with a sliding door 142. When the door 142 is closed, the slot 144 is sealed and a low flow rate may be measured. When the door 142 is open, more exhaled air escapes so that greater effort is required to move the indicator in the body. In another embodiment, the door 142 may have more than two positions corresponding to different desired flow rates.

The peak flow meter 130 preferably has interchangeable windows that snap fit into a window slot on the body. One window preferably includes a logarithmic scale with an expanded scale for low flow rate measurements. The low flow rate scale may be used with the peak flow meter 130 adjusted so that the door 142 of the bias vent 140 is closed. A higher flow rate window may replace the low flow rate window when the peak flow meter is adjusted so that the door 142 is open. The higher flow rate window preferably includes a less compressed logarithmic scale. The interchangeable windows and the bias vent 140 are advantageous for making the peak flow meter 130 more adaptable for use by adults and children.

Figure 19:
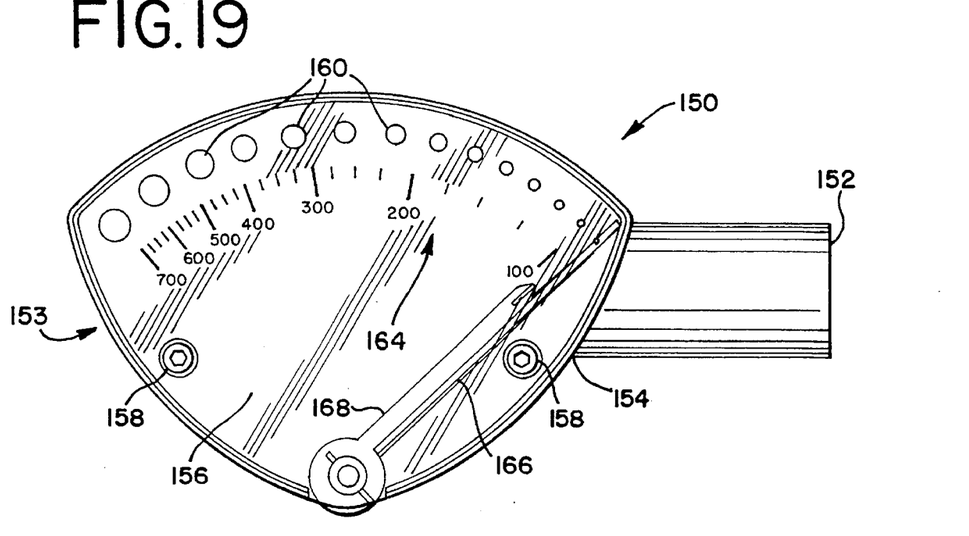
FIG. 19 is a left side view of a fourth embodiment of a peak flow meter in accordance with the present invention.

FIG. 19 illustrates a fourth preferred embodiment of a peak flow meter 150. FIG. 19 shows a peak flow meter having an inlet area 152 and an outlet area 153 on a curved hollow body 154. A window 156 covers one side of the body 154. The window 156 is preferably a clear plastic material attached to the body 154 with a pair of fasteners 158, such as screws or bolts.

Figure 20:
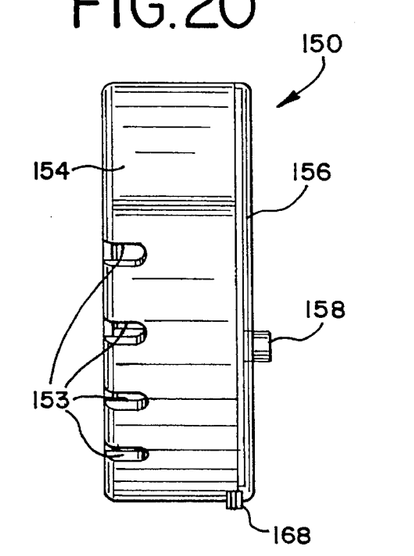
FIG. 20 is a rear view of the peak flow meter of FIG. 19.
Figure 21:
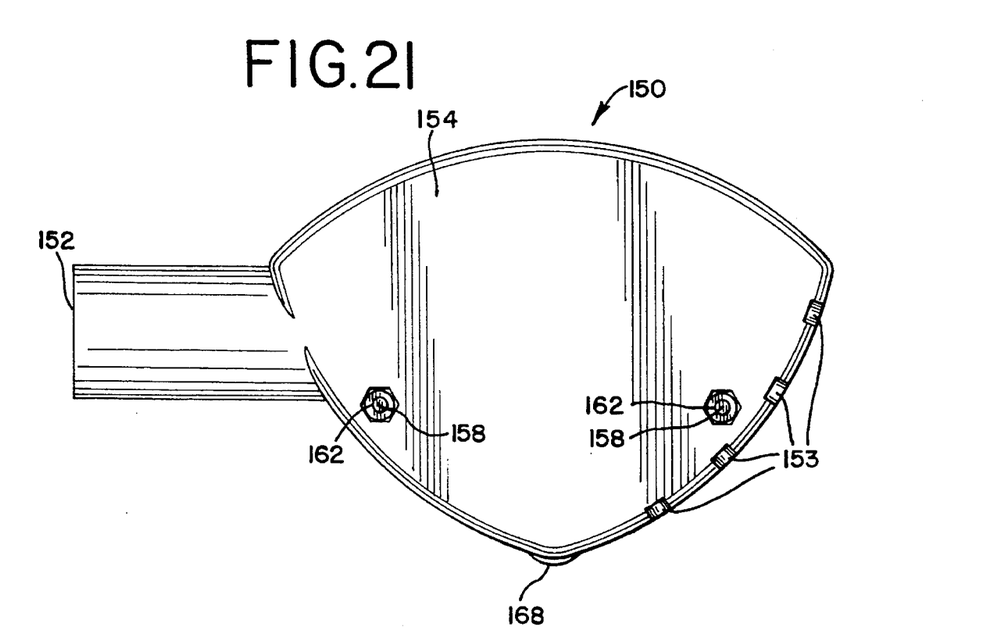
FIG. 21 is a right side view of the peak flow meter of FIG. 19.
Figure 22:
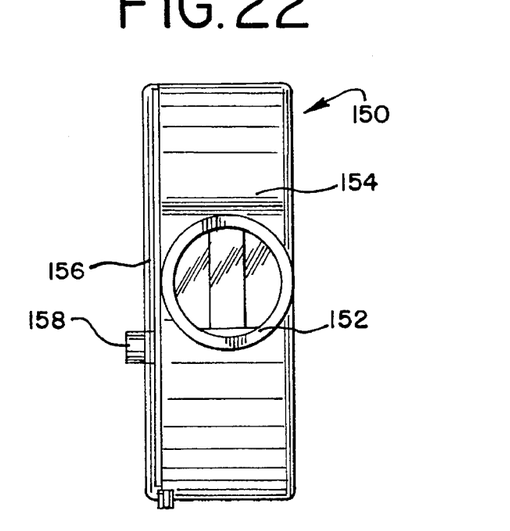
FIG. 22 is a front view of the peak flow meter of FIG. 19.

FIG. 20 shows a rear view of the peak flow meter 150. The outlet area 153 preferably comprises at least one opening in the rear of the body 154. FIG. 21 provides another side view of the peak flow meter. As is best seen in FIG. 21, the fasteners 158 are secured by a pair of anchors 162, such as a threaded portion in the body or bolts. As shown in FIG. 22, the inlet 152 is preferably a hollow tube integral with the body 154.

Referring again to FIG. 19, the window 156 preferably includes a plurality of vents 160 that increase in size from the inlet 152 to the outlet 153. Also on the window 156 is a logarithmic scale 164. The logarithmic scale 164 may be printed or molded on the inside or outside of the window. A rigid vane 166 and an indicator 168 are mounted inside the hollow body 154 and window. Both the vane 166 and indicator 168 are frictionally coupled to the body and window at the base of the peak flow meter 150. The vane releasably engages the indicator when a patient exhales into the inlet of the peak flow meter 150.

Figure 23:
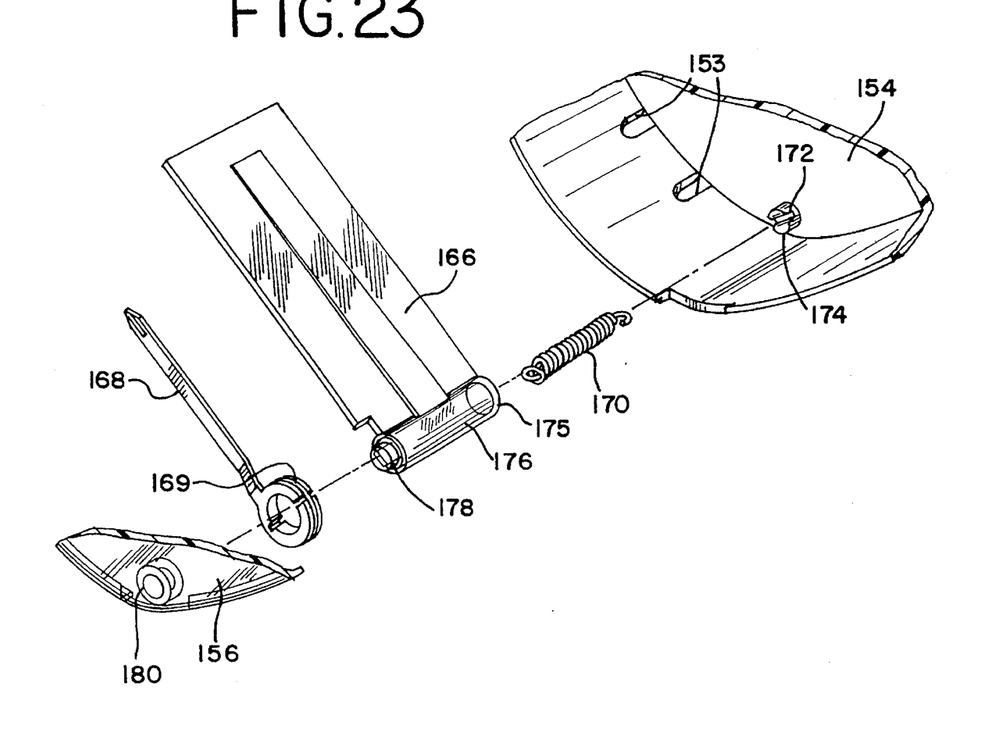
FIG. 23 is a fragmentary exploded view of the peak flow meter of FIG. 19.

This embodiment of the peak flow meter preferably operates using a torsion spring 170 which is best shown in FIG. 23. The spring 170 removably connects with a slot 172 in a vane coupling tab 174 that is attached to the interior of the body 154. When the open end 175 of the hollow cylinder 176 at the base of the vane 166 is pressed over the vane coupling tab 174, the spring 170 also removably connects to a slot inside the cylinder 176. An indicator 168 slidably fits around a protruding ring 180 on the interior of the window 156. The cylindrical plug 178 on the vane 166 slidably fits into the center of the protruding ring 180. Assembled, the vane 166 is positioned between the indicator and the inlet 152.

The inlet receives exhaled air from a patient. The exhaled air pushes the rigid vane against the indicator. Both the vane and the indicator rotate in the plane of the window about the joint created by the assembly of the vane coupling tab 174, the protruding ring 180, the cylinder 176 and the cylindrical plug 178. The spring 170, which is removably attached to the body 154 and the vane, provides resistance to air exhaled into the inlet against the rigid vane. The plurality of vents 160 in the window are empirically designed to cooperate with the resistance force of the spring so that the indicator's response conforms with a logarithmic scale 164 on the body.

In an alternative embodiment, the plurality of vents may be eliminated by or used in combination with changing the shape of the body and window. The shape may be changed to non-linearly increase the gap between the vane and the body or window thereby increasing the force necessary to move the indicator as it is pushed along the scale 164. As with the plurality of vents, the increased gap is empirically designed so that the indicator's position conforms to a logarithmic scale on the Window. In another embodiment of the peak flow meter 150, the torsion spring 170 may be used with a flexible vane to achieve the desired indicator movement.

After a peak flow of air has caused the vane to push the indicator, the vane 166 returns to its rest position under the force of the spring 170. The indicator 168 remains in the position to which it was moved by the vane and is held in place by friction against the protruding ring 180. The friction is maintained by a split wire coil 169 surrounding the base of the indicator 168. The indicator 168 may be returned to a rest position by rotating the exposed portion of the indicator 168 on the bottom of the peak flow meter 150. As with previously described embodiments, an advantage of using the logarithmic scale is that it may be used in combination with an assessment tape that will indicate the same percentage deviation below any given peak flow measurement regardless of placement along the scale. The assessment tape may be manufactured to conform with any constant scale curvature on the peak flow meter.

Other alternative preferred techniques for attaining a response to peak air flow that conforms to a logarithmic scale are included in the present invention. A variable response spring, whether torsion or expansion, is one technique. The spring coil diameter may be gradually increased so that the force varies non-linearly. Another technique is the use of a flexible piston that flexes to permit greater amounts of air to pass as the force of the air against it increases. Additionally, the hollow slotted tube carrying the indicator may be constructed such that the friction between the indicator and the tube increases as the indicator is pushed further down the tube. These techniques may be used individually or in combination with each other so that the indicator's response to a peak flow of exhaled air conforms with a chosen logarithmic scale.

From the foregoing, an improved peak flow meter has been described. The peak flow meter includes at least one vent, and alternatively a plurality of vents, for obtaining a logarithmic response to exhaled air. An assessment tape cooperates with a logarithmic scale for simple, accurate and informative measurements of a patient's peak flow. Additionally, an adaptable peak flow meter has been described that is useful for low flow and high flow applications.

It is intended that the foregoing detailed description be regarded as illustrative rather than limiting, and that it be understood that the following claims, including all equivalents, are intended to define the scope of this invention.

I claim:

1. A peak flow meter comprising:
   a body for accommodating a flow of exhaled air therethrough;
   an indicator associated with said body and movable relative to said body to a position along a logarithmic scale on said body, said position related to a peak flow of air exhaled through said body; and
   said body having a plurality of vents positioned along the body and allowing air to escape the body such that said indicator's position in response to the peak flow of exhaled air conforms to said logarithmic scale.

2. The peak flow meter of claim 1 wherein said indicator is completely enclosed within said body.

3. The peak flow meter of claim 1 wherein said indicator is slidably mounted on a hollow slotted tube inside said body.

4. The peak flow meter of claim 3 further comprising a piston slidably mounted on said hollow slotted tube for releasably engaging said indicator.

5. The peak flow meter of claim 1 further comprising a bendable vane mounted in said hollow body for releasably engaging said indicator.

6. The peak flow meter of claim 1 wherein said body further comprises a sample channel and at least one bypass channel.

7. The peak flow meter of claim 6 wherein said plurality of vents are positioned between said sample channel and said at least one bypass channel.

8. The peak flow meter of claim 6 wherein said plurality of vents are positioned along said sample channel.

9. The peak flow meter of claim 6 wherein said sample channel is parallel to said at least one bypass chamber.

10. The peak flow meter of claim 6 wherein said sample channel is positioned at an angle relative to the at least one bypass channel.

11. The peak flow meter of claim 1 further comprising a rigid vane removably attached to a torsion spring for releasably engaging said indicator.

12. The peak flow meter of claim 1 wherein said body further comprises a detachable snap fit window positioned over said indicator.

13. The peak flow meter of claim 12 wherein said window includes a logarithmic scale integral to the window.

14. A peak flow meter system comprising:
    a peak flow meter having a hollow body for accommodating a flow of air exhaled therethrough, an indicator associated with said body responsive to said flow of air and movable relative to said body to a position along said body, said position related to a peak flow of air, said body having a plurality of vents distributed on the body, said vents defining openings in the body that allow air to escape the body such that the position of the indicator in response to the peak flow of air conforms to a logarithmic scale on the body; and
    an assessment tape, said assessment tape attachable to said body on said scale.

15. A peak flow meter adaptable for measuring low and high peak flow rates comprising:
    a hollow body for accommodating a flow of exhaled air therethrough;
    an indicator associated with said body and movable relative to said body to a position along a scale on said body, said position related to a peak flow of air exhaled through said body;
    said body having a plurality of vents distributed on the body and allowing an amount of air to escape the body such that said scale represents a logarithmic scale of the peak flow of air exhaled through said body; and said body having a bias vent for adapting the peak flow meter to selectively measure high and low flow rates.

16. The peak flow meter of claim 15 wherein said body further comprises:

a window slot positioned over said indicator; and a removable snap-fit window having a scale for cooperating with said bias vent and adapting the flow rate measurement range.

17. A peak flow meter having a hollow horizontal section including an inlet for receiving a flow of exhaled air, an outlet, and a bypass channel connecting the inlet and the outlet; and a hollow vertical section connected to the hollow horizontal section including a sample channel for receiving a portion of the air exhaled into the inlet, an indicator, a piston for moving the indicator in response to the portion of exhaled air, a scale for reading a position of the indicator, and a vertical section outlet;

wherein the improvement comprises:

at least one vent positioned on said vertical section allowing a determined amount of air to escape the vertical section such that said indicator's position in response to the flow of exhaled air conforms to said scale, and wherein the scale is a logarithmic scale of a peak flow of the air exhaled into the inlet.

18. A peak flow meter having a hollow body including an inlet for receiving a flow of exhaled air;

an outlet;

a sample channel inside the body;

at least one bypass channel parallel to the sample channel;

an indicator positioned in the sample channel;

a piston positioned in the sample channel for moving the indicator in response to the flow of exhaled air; and a scale positioned on the body for reading a position of the indicator;

wherein the improvement comprises:

at least one vent positioned along the sample channel, said at least one vent allowing an amount of air to escape the sample channel such that the response of the piston and indicator to a peak flow of the exhaled air corresponds to the scale on the body, and wherein the scale is a logarithmic scale of a peak flow of the air exhaled into the inlet.

19. A peak flow meter having a hollow body including an inlet for receiving a flow of exhaled air, an outlet, a bendable vane mounted inside said hollow body, said bendable vane for moving an indicator to a position inside said body in response to a peak flow of exhaled air, and a scale on the body for measuring a position of said indicator, wherein the improvement comprises:

at least one vent positioned on said body, said at least one vent allowing an amount of air to escape the body so that the indicator's position in response to a peak flow of the exhaled air conforms to the scale, and wherein said scale is a logarithmic scale of the peak flow of the air exhaled into said inlet.

20. A peak flow meter having a hollow body including an inlet for receiving a flow of exhaled air, an outlet, a window, a rigid vane removably attached to a torsion spring inside said hollow body and said window, said rigid vane for moving an indicator inside said body in response to a peak flow of exhaled air, and a scale on the body for measuring a position of said indicator, wherein the improvement comprises:

at least one vent positioned on said body, said at least one vent allowing an amount of air to escape the body such that the position of the indicator in response to the peak flow of air is a logarithmic representation of the peak flow of air into said inlet, and wherein said scale is a logarithmic scale.

\* \* \* \* \*

UNITED STATES PATENT AND TRADEMARK OFFICE
CERTIFICATE OF CORRECTION

PATENT NO. : 5,565,630
DATED : October 15, 1996
INVENTOR(S) : William R. Shene

It is certified that error appears in the above-indentified patent and that said Letters Patent is hereby corrected as shown below:

On the title page,

In column 1, before line 1, "UNDER U.S. PATENT DOCUMENTS", please insert a new line as follows:

--4,227,409   10/1980   Bingler   73/861.71--.

In column 1, line 4, "UNDER U.S. PATENT DOCUMENTS", replace "73/17.9" with --73/709--.

In column 2, line 3, "UNDER OTHER PUBLICATIONS", after "Best" insert --Peak--.

In page 2, column 1, line 2, "UNDER U.S. PATENT DOCUMENTS", replace "4,292,775" with --4,287,775--.

UNITED STATES PATENT AND TRADEMARK OFFICE
CERTIFICATE OF CORRECTION

PATENT NO. : 5,565,630
DATED : October 15, 1996
INVENTOR(S) : William R. Shene

It is certified that error appears in the above-indentified patent and that said Letters Patent is hereby corrected as shown below:

In page 2, column 1, line 7, "UNDER U.S. PATENT DOCUMENTS", replace "1/1981" with --1/1987--.

In page 2, column 2, line 1, "UNDER OTHER PUBLICATIONS", replace "Vitalograph" with --"Vitalograph"--.

In page 2, column 2, line 2 "UNDER OTHER PUBLICATIONS", replace "of" with --For--.

Signed and Sealed this

Seventh Day of July, 1998

*Attest:*

*Attesting Officer*

BRUCE LEHMAN

*Commissioner of Patents and Trademarks*